(12) United States Patent
Schnell et al.

(10) Patent No.: US 10,251,979 B2
(45) Date of Patent: Apr. 9, 2019

(54) IMPLANTABLE ACCESS DEVICE AND METHOD FOR PREPARING THEREOF

(75) Inventors: Andrea Schnell, Bisingen-Thanheim (DE); Bernd Wittner, Hechingen (DE); Claudia Hildwein, Voehringen (DE); Ruth Dietrich, Hechingen (DE); Reinhold Deppisch, Hechingen (DE); Doris Deppisch, legal representative, Hechingen (DE); Werner Beck, Rottenburg (DE)

(73) Assignee: GAMBRO LUNDIA AB, Lund (SE)

( * ) Notice: Subject to any disclaimer, the term of this patent is extended or adjusted under 35 U.S.C. 154(b) by 0 days.

(21) Appl. No.: 11/993,663

(22) PCT Filed: Jun. 12, 2006

(86) PCT No.: PCT/SE2006/000683
§ 371 (c)(1),
(2), (4) Date: Aug. 11, 2010

(87) PCT Pub. No.: WO2006/137768
PCT Pub. Date: Dec. 28, 2006

(65) Prior Publication Data
US 2011/0015720 A1 Jan. 20, 2011

Related U.S. Application Data

(60) Provisional application No. 60/694,879, filed on Jun. 29, 2005.

(30) Foreign Application Priority Data

Jun. 23, 2005 (SE) .................................. 0501503-7

(51) Int. Cl.
*A61L 31/00* (2006.01)
*A61L 31/02* (2006.01)
(Continued)

(52) U.S. Cl.
CPC ............. *A61L 31/022* (2013.01); *A61L 31/14* (2013.01); *A61M 39/0208* (2013.01);
(Continued)

(58) Field of Classification Search
CPC .. A61M 39/02; A61M 39/04; A61M 39/0208; A61M 2039/0205;
(Continued)

(56) References Cited

U.S. PATENT DOCUMENTS 2,942,520 A * 6/1960 Rose .............................. 359/398
3,065,669 A * 11/1962 Orsi .............................. 359/398
(Continued)

FOREIGN PATENT DOCUMENTS

WO 97/47338 A1 12/1997
WO 98/31272 A2 7/1998
(Continued)

OTHER PUBLICATIONS

Communication pursuant to Article 94(3) EPC in the related EP 06 77 876.8-1660 dated Jul. 8, 2013, 4 pages.

*Primary Examiner* — Scott J Medway
(74) *Attorney, Agent, or Firm* — Barnes & Thornburg LLP

(57) ABSTRACT

The present invention concerns an implantable access device and a method for preparing the device. According to the invention the device comprises a shape memory base structure with a biological substructure suitable for cell adhesion, cell engraftment and proliferation for use in transferring and transporting fluid mixtures (blood, suspensions, drug formulations, emulsions, cell suspensions) in/into/out of a human or animal body.

13 Claims, 7 Drawing Sheets

(51) Int. Cl.
*A61L 31/14* (2006.01)
*A61M 39/02* (2006.01)
*A61M 39/26* (2006.01)

(52) U.S. Cl.
CPC .......... *A61M 39/26* (2013.01); *A61L 2400/16* (2013.01); *A61M 2039/0202* (2013.01); *A61M 2039/0205* (2013.01); *A61M 2039/0223* (2013.01); *A61M 2205/0266* (2013.01)

(58) Field of Classification Search
CPC ..... A61M 2039/02111; A61M 39/0247; A61F 2/0077; A61L 29/146
USPC .... 424/443, 78, 81, 484, 486; 435/174, 180, 435/240.2, 240.23, 240.241
See application file for complete search history.

(56) References Cited

U.S. PATENT DOCUMENTS

| | | | | |
|---|---|---|---|---|
| 3,928,142 | A * | 12/1975 | Smith | 435/284.1 |
| 4,299,920 | A * | 11/1981 | Peters | 435/288.4 |
| 4,308,351 | A * | 12/1981 | Leighton et al. | 435/297.5 |
| 4,321,914 | A | 3/1982 | Begovac et al. | |
| 4,488,877 | A * | 12/1984 | Klein | A61M 1/285 |
| | | | | 604/175 |
| 4,543,088 | A | 9/1985 | Bootman et al. | |
| 4,634,422 | A | 1/1987 | Kantrowitz et al. | |
| 4,734,372 | A * | 3/1988 | Rotman | 435/29 |
| 4,781,695 | A * | 11/1988 | Dalton | A61M 39/0208 |
| | | | | 604/175 |
| 4,866,011 | A * | 9/1989 | Hargus et al. | 501/82 |
| 4,886,501 | A * | 12/1989 | Johnston | A61M 39/0208 |
| | | | | 604/175 |
| 5,037,656 | A * | 8/1991 | Pitt et al. | 424/443 |
| 5,039,340 | A * | 8/1991 | Hargus et al. | 501/81 |
| 5,092,849 | A * | 3/1992 | Sampson | A61M 39/0208 |
| | | | | 604/175 |
| 5,100,392 | A | 3/1992 | Orth et al. | |
| 5,242,415 | A | 9/1993 | Kantrowitz et al. | |
| 5,281,199 | A * | 1/1994 | Ensminger | A61M 39/0208 |
| | | | | 604/288.03 |
| 5,478,739 | A * | 12/1995 | Slivka et al. | 435/399 |
| 5,693,088 | A * | 12/1997 | Lazarus | A61F 2/07 |
| | | | | 606/195 |
| 5,704,915 | A * | 1/1998 | Melsky | A61M 39/0208 |
| | | | | 604/175 |
| 5,741,228 | A * | 4/1998 | Lambrecht | A61M 39/0208 |
| | | | | 251/149.3 |
| 5,848,989 | A * | 12/1998 | Villani | A61M 39/0208 |
| | | | | 604/175 |
| 5,861,035 | A | 1/1999 | Griffith | |
| 6,013,051 | A * | 1/2000 | Nelson | A61M 39/0208 |
| | | | | 604/247 |
| 6,013,855 | A * | 1/2000 | McPherson et al. | 623/23.76 |
| 6,904,658 | B2 * | 6/2005 | Hines | 29/423 |
| 6,916,652 | B2 * | 7/2005 | Petrecca et al. | 435/286.5 |
| 6,962,577 | B2 * | 11/2005 | Tallarida | A61M 39/0208 |
| | | | | 604/288.02 |
| 7,311,727 | B2 * | 12/2007 | Mazumder et al. | 623/1.44 |
| 7,458,987 | B2 * | 12/2008 | Case et al. | 623/1.24 |
| 7,713,297 | B2 * | 5/2010 | Alt | 623/1.39 |
| 2002/0177823 | A1 | 11/2002 | Prosl et al. | |
| 2003/0199887 | A1 * | 10/2003 | Ferrera et al. | 606/151 |
| 2003/0220552 | A1 * | 11/2003 | Reghabi | A61B 5/14532 |
| | | | | 600/365 |
| 2004/0204686 | A1 | 10/2004 | Porter et al. | |
| 2005/0123582 | A1 * | 6/2005 | Sung et al. | 424/426 |
| 2006/0282166 | A1 * | 12/2006 | Molz et al. | 623/17.13 |
| 2008/0171944 | A1 * | 7/2008 | Brenneman | A61B 17/11 |
| | | | | 600/509 |
| 2008/0294096 | A1 * | 11/2008 | Uber et al. | 604/66 |
| 2009/0024158 | A1 * | 1/2009 | Viker | A61B 17/0206 |
| | | | | 606/201 |
| 2009/0076466 | A1 * | 3/2009 | Quebbemann | A61M 29/00 |
| | | | | 604/288.02 |
| 2009/0123435 | A1 * | 5/2009 | Ratcliffe et al. | 424/93.7 |
| 2010/0184183 | A1 * | 7/2010 | Schussler et al. | 435/177 |
| 2011/0015720 | A1 * | 1/2011 | Schnell et al. | 623/1.15 |

FOREIGN PATENT DOCUMENTS

| | | |
|---|---|---|
| WO | 98/51368 A1 | 11/1998 |
| WO | 99/20338 A1 | 4/1999 |
| WO | 99/34852 A1 | 7/1999 |
| WO | 00/40282 A1 | 7/2000 |
| WO | 01/32141 A1 | 5/2001 |
| WO | 03/035278 A1 | 5/2003 |
| WO | 2004/103425 A1 | 12/2004 |
| WO | 2005/037055 A2 | 4/2005 |

* cited by examiner

IMPLANTABLE ACCESS DEVICE AND METHOD FOR PREPARING THEREOF

CROSS REFERENCE TO RELATED APPLICATION

This application is a national phase application based on PCT/SE2006/000683, filed Jun. 12, 2006, which claims the priority of Swedish Patent Application No. 0501503-7, filed Jun. 23, 2005, and the benefit of U.S. Provisional Application No. 60/694,879, filed Jun. 29, 2005, the contents of all of which are incorporated herein by reference.

TECHNICAL FIELD

The present invention concerns an implantable access device and a method for preparing thereof. More particular it relates to an implantable medical device to create a transcutaneous access to organ and vascular systems.

BACKGROUND OF THE INVENTION

Within the prior art, a couple of different transcutaneous vascular access systems are disclosed, of which some are disclosed in WO 01/032141, WO 97/047338, WO00/40282, WO 99/020338, WO 98/31272, WO 98/51368, WO 99/34852, U.S. Pat. Nos. 4,321,914 and 4,543,088. However, many of these have entered clinical practice with contradictory and pivotal results. The main problems raising is this context, i.e. infections, biofilm, device failure after repeated use to high for routine applications.

The drawbacks of prior art are clearly related to enhanced risk of infection mainly pocket infection around the implant. Due to repeated puncture, the integrity of the skin is resolved and bacteria can penetrate in the space between the artificial device and surrounding tissue. If an inflammatory process is started, the fibrosis response is enhanced and therefore a fibrous capsule around the implant is created. Bacteria will fill the intermediate phase between the fibrous cap and the surface of the implanted device over time and a biofilm is developing which finally leads to repeatedly occurring serious infections. This can only be treated by direct injection of antibiotics or disinfections fluids. Basically people are using lavage techniques as applied for major wound care, e.g. by applying fluids containing antibiotics or e.g. taurolidine. Due to the high risk of infection and deposition of bacteria, the risk for coagulation in the device is also increasing. Patients being dependent on these devices are exposed to a great risk to get severe infection complications, e.g. sepsis which may lead to long hospitalisation or even death of the patient. In addition, usually such access devices are used for patients where the vascular alternatives for blood access, i.e. vascular sites for new access constructions, are exhausted and the creation of a port system is the ultimate solution to get blood access needed for life saving extracorporeal therapies. If problems arise there is a great risk that the transcutaneous vascular access system has to be removed, which makes a further extracorporeal treatment more difficult or even impossible.

Accordingly, the main problems with these systems are that (i) the procedures to place these devices are difficult and frequently demanding revision of the access, committant and prophylactic use of antibiotics and disinfectants or major surgery, (ii) they easily give rise to infections and especially pocket infections around the devices, (iii) they have an inconsistent care hygiene and (iv) they require a relatively complex connection procedure. It is obvious that the state of the art devices missing important biological process enabling routine and medically acceptable access. Although these infections are treatable by lavage or antibiotics, this give rise to skin erosion, compromised wound healing, trauma relieve, and skin damage by repeated disinfections, entering a vicious circle of infections, bad healing, followed skin erosion, etc.

SUMMARY OF THE INVENTION

One object of the present invention is to provide a device that will preserve the integrity of the skin to thereby avoid the primary problem of pocket infection and by this breaking the vicious circle at defined and advantageous level. The present invention relates to an implantable access device. According to the invention the device comprises a shape memory base structure with a substructure suitable for cell adhesion, cell engraftment and proliferation, which device could be used for transferring fluid into/out of a human or animal body. According to the invention the shape memory base structure together with the substructure allows for a 3-dimensional fixation and integration of cells on and within the access device. The substructure is designed to support a accelerated or normal wound healing process.

In one embodiment of the invention said device has a base structure with openings in the range of at least 30 µm and at most 10 mm. In another embodiment said openings are at most 3 mm, and in even another embodiment at most 300 µm.

In another embodiment said base structure allows formation of a substructure with openings in the range of 1-30 µm, and in one embodiment said substructure has filaments in the range of 0.1 to 5 µm, and the filaments are monofilaments or multifilaments.

In even additional embodiments said substructure is a biological or synthetic polymeric substructure, wherein said polymeric substructure comprises at least one of fibrin, plasma, platelet rich plasma, collagen, serum components, polyelectrolytes, hyaluronic acid, glycosaminoglycan, polyglucose, chitosan, alginate, polylactic acid, polyglycolic acid, polygluconic acid or mixtures thereof. (e.g. fibrin net formed out of plasma or platelet rich plasma or fibrin net formed out of precursor components).

In another embodiment said polymeric material above for the substructure could be mixed with typical connective tissue component, such as laminin, decorin, etc.

In one embodiment said shape memory base structure comprises a shape memory and/or elastic material. This material is chosen from the group comprising shape memory material, such as shape memory metallic alloy material, stainless steel, polymeric shape memory material, polygluconic acid, polyglycolic acid, polylactic acid, and collagen.

Further, said base structure has filaments in the range of 10 to 1000 µm, and these filaments are monofilaments or multifilaments. In even further embodiments, said base structure is braided, woven, foamed, and/or knitted.

In one embodiment said device comprises a generally conical body portion having a receptor end adapted to receive a needle and a positioning end adapted to position the end of said needle. In an additional embodiment said receptor end is wider than said positioning end.

In one embodiment said device is capable of receiving needles from a number of discrete puncture points at the receptor end, and is capable of guiding a needle from each puncture points at the receptor end to the positioning end of the body portion.

In another embodiment, said device further is capable of receiving needles from a number of discrete puncture points at the receptor end, and is capable of guiding a needle from each discrete puncture points at the receptor end to a discrete positioning end for each puncture point, respectively.

In one embodiment said device further comprises an opening/closing mechanism that operates to prevent fluid flow through the device when not in use.

In a further embodiment said opening/closing mechanism is adapted to open when a needle is introduced into and bears upon said body portion positioning end. In one embodiment said opening/closing mechanism is operating as a valve.

In one embodiment said device is connected in the positioning end to a (vascular or artificial) graft.

In another embodiment, said device is connected in the positioning end to a vascular stent construction.

In even another embodiment said device is connected in the positioning end with a permanent catheter tube(s).

The present invention further relates to a method for preparing an implantable access device according to any of the embodiment above. According to the invention, the method involves the steps of a) preparing the device by having a substructure to adhere on the base structure, to prepare a substructure with openings in the range of 1-30 µm, and thereafter b) initiate culturing of tissue cells, connective tissue cells, normal human dermal fibroblasts, epithelial cells, epidermal cells, endothelial cells, and/or stem cells (as well as suitable mixture cultures) onto and into the prepared device. In one embodiment of the method, said substructure comprises direct attachment as a 3-dimensional network of fibrin, plasma, platelet rich plasma, collagen, serum components, polyelectrolytes, hyaluronic acid, glycosaminoglycan, polyglucose, chitosan, alginate, polyelectrolytes, polylactic acid, polyglycolic acid, polygluconic acid. or mixtures thereof. By this, a 3-dimensional and functional network structure is constructed, enabling tissue cell biology as well as required bio-mechanical properties.

In another embodiment, the method further comprises that before preparing the device, the base structure is treated with a biological material to enhance the binding and formation of the substructure. In one embodiment said biological material is plasma or platelet rich plasma (PRP).

In even another embodiment, the method further comprises the step in which stem cells and thereof derived supernatants or growth factors are added either when preparing said substructure or when initiating culturing of tissue cells, connective tissue cells, normal human dermal fibroblasts, epithelial cells, epidermal cells, endothelial cells, and/or stem cells. In one embodiment the stem cells are mesenchymal stem cells and/or vascular progenitor cells.

The device according to the invention is to be implanted subcutaneously as a permanent device. In comparison to other port systems, the implant according to the invention will be completely and biologically compatible integrated into the connective tissue, and cells will grow within the whole access device in order to let the access device become filled with tissue material. To achieve this the access device will be seeded with autologous connective tissue cells or (mesenchymal) stem cells or both before the implantation. Due to the integration of autologous skin cells or (mesenchymal) stem cells various improvements concerning biocompatibility and tissue functionality is implement, such as the risk of immune response can be drastically reduced and functional disarrangement of the skin in the different skin and tissue layers above the implant can be prevented. This means that the natural protection function of the skin, i.e. mechanical properties or secretion of antibacterial barrier function, may be re-established.

Definitions

The term shape memory is intended to mean that it is made of a material that after a geometrical reorientation, either by physical cause or by other type of causes, regains it original shape when the reorientation force is removed/inactivated. Accordingly, this could be an elastic material, which regains it's original shape after removal of reorientation force, and it could be a shape memory alloy material, which widens and shrinks due to e.g. temperature changes, or it could be a combination thereof.

The term biological polymeric substructure is intended to mean biological polymeric material that is able to form substructures suitable for adherence of tissue cells, connective tissue cells, normal human dermal fibroblasts, epithelial cells, epidermal cells, endothelial cells, and/or stem cells. Examples of biological polymeric materials are fibrin, plasma, platelet rich plasma, collagen, serum components, polyelectrolytes, hyaluronic acid, glycosaminoglycan, polyglucose, chitosan, alginate or mixtures thereof.

The term synthetic polymeric substructure is intended to mean a synthetic polymeric material that is able to form a substructure suitable for adherence of tissue cells, connective tissue cells, normal human dermal fibroblasts, epithelial cells, epidermal cells, endothelial cells, and/or stem cells. Examples of synthetic polymeric materials are polyelectrolytes, polylactic acid, polyglycolic acid, and polygluconic acid.

Both the base structure and the substructure could be made of a biodegradable or biostable or bioinert polymer.

The term plasma is intended to mean the plasma protein fraction separated by centrifugation or filtration from the cellular blood components, i.e. removal of all cellular fractions from whole blood.

The term platelet rich plasma (PRP) is intended to mean the plasma protein fraction additionally containing platelets separated by centrifugation or filtration from white blood cells and red blood cell fraction.

BRIEF DESCRIPTION OF THE DRAWING(S)

DETAILED DESCRIPTION OF THE INVENTION

The access device according to the invention consists of a shape memory base structure with a substructure suitable for cell adhesion, cell engraftment and proliferation for use in transferring fluid into/out of a human or animal body or transporting fluids in the body.

The base structure with the shape memory or elastic structure allows an inbuilt mechanism that after the puncturing process, which is after removal of a needle, the skin construct is automatically moved back to the initial structure. By this the skin function and wound healing is enhanced, the bleeding after removal of the needle is reduced and with respect to therapeutic application or requirements of a vascular access system a reduced risk for invasion of bacteria and fibrous scar tissue formation can be achieved. Furthermore, there is support of the skin by the shape memory base material, which increases the resistance of the tissue against manipulations and movement in daily life as well as during application.

The material in the base structure could be a shape memory material, an elastic shape memory material or an elastic material. It should allow introduction of a needle therein, but most important is that the base material has the feature of having a driving force or ability to regain the geometry shape of the access device after removal of a needle. By this driving force or ability to regain the geometry shape, the base structure takes over the mechanical integrity of the tissue during reconstruction in tissue healing and revascularisation phase, i.e. closing openings, channels formed during puncture.

On the base structure a substructure is to be formed. This substructure provides basically two functions, 1) tailored distance between openings in a network, and 2) allowing anchoring, cell supporting and intrusion of cells and formation of multiple pseudopodia to get a 3-dimensional (3-D) fixation or integration of cells on and within the access device according to the invention.

Accordingly, the access device according to the invention has a base structure and a substructure which allows ingrowth of cells into the whole access device in order to let the access device become filled with tissue material. In this way the puncturing is made with a needles which is guided through the tissue within the access device to a positioning end for blood access, after removal of the needle the shape memory base structure helps the skin tissue to regain the original geometric shape to thereby close the channels formed in the tissue during puncture.

Figure 3:
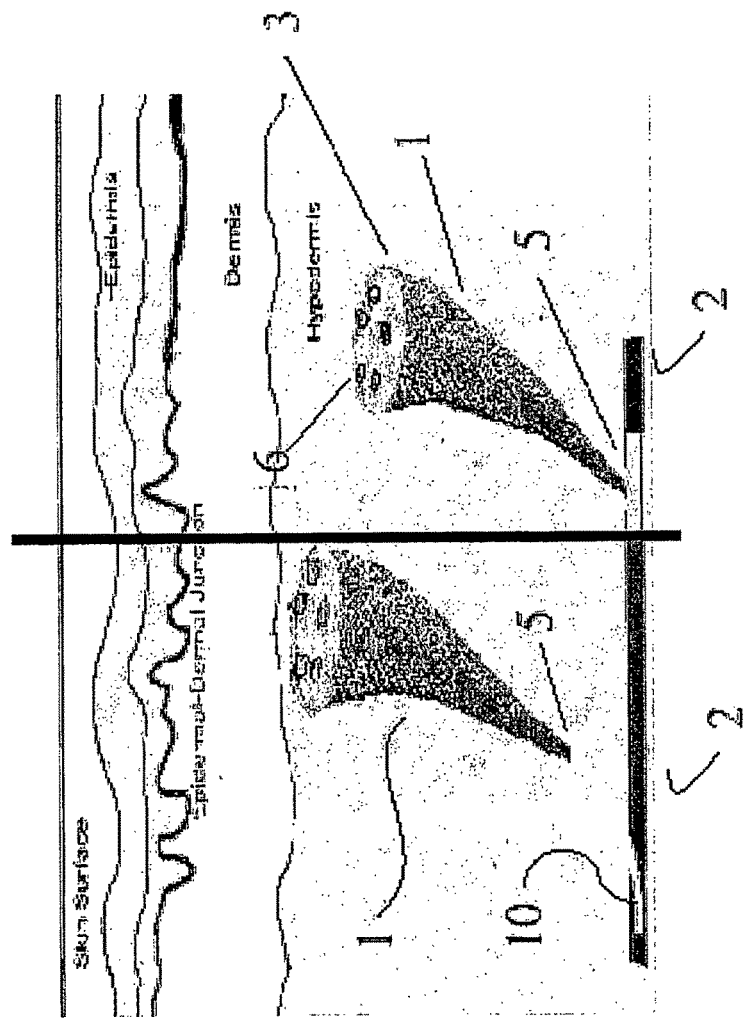
FIG. 3 shows the access device according to the invention implanted with two different techniques in the hypodermis.
Figure 4:
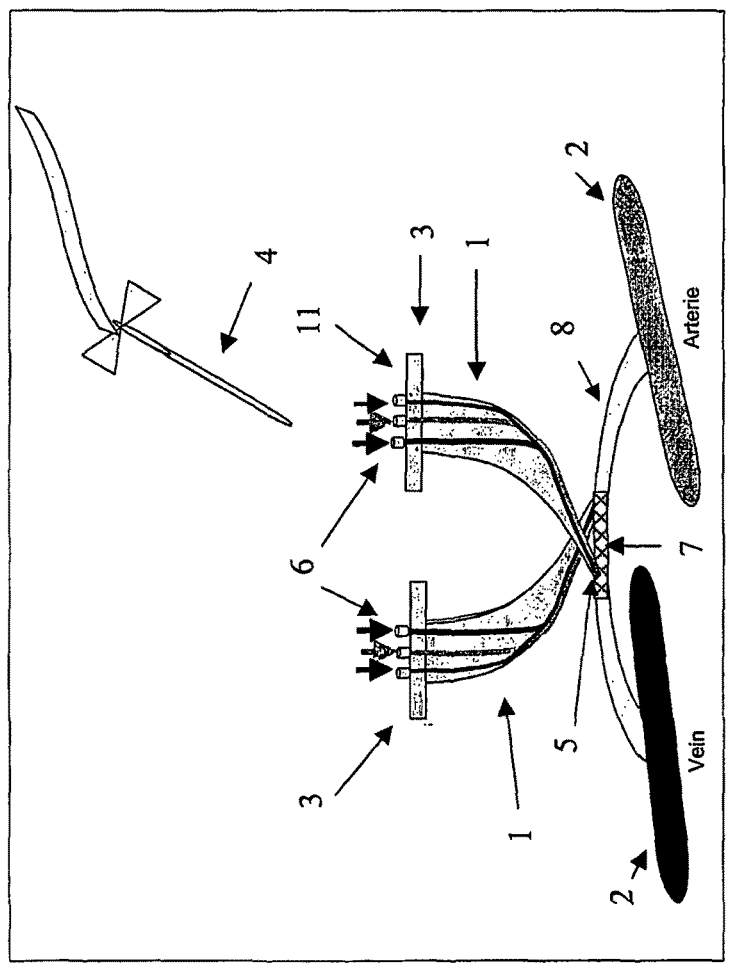
FIG. 4 shows one embodiment of the access device according to the invention integrated and fixed to the outer surface of a graft.

The access device according to the invention should be subcutaneously implanted as a permanent device. The device (1) is preferably implanted in the hypodermis layer and arranged to enter the vessel system (2), see e.g. FIGS. 3 and 4. As stated above, said device (1) has a body portion with a receptor end (3) adapted to receive a needle (4) and a positioning end (5) adapted to position the end of said needle (4).

In one embodiment of the access device according to the invention the receptor end (3) is adapted to receive needles (4) from a number of discrete puncture points (6). In even an additional embodiment this is provided by having an entry member (11) containing a plurality of apertures (6), wherein each aperture (6) is adapted to receive a needle (4) that has passed through overlaying skin. In one embodiment this entry member is a sheet (11) having a plurality of apertures (6).

Figure 5:
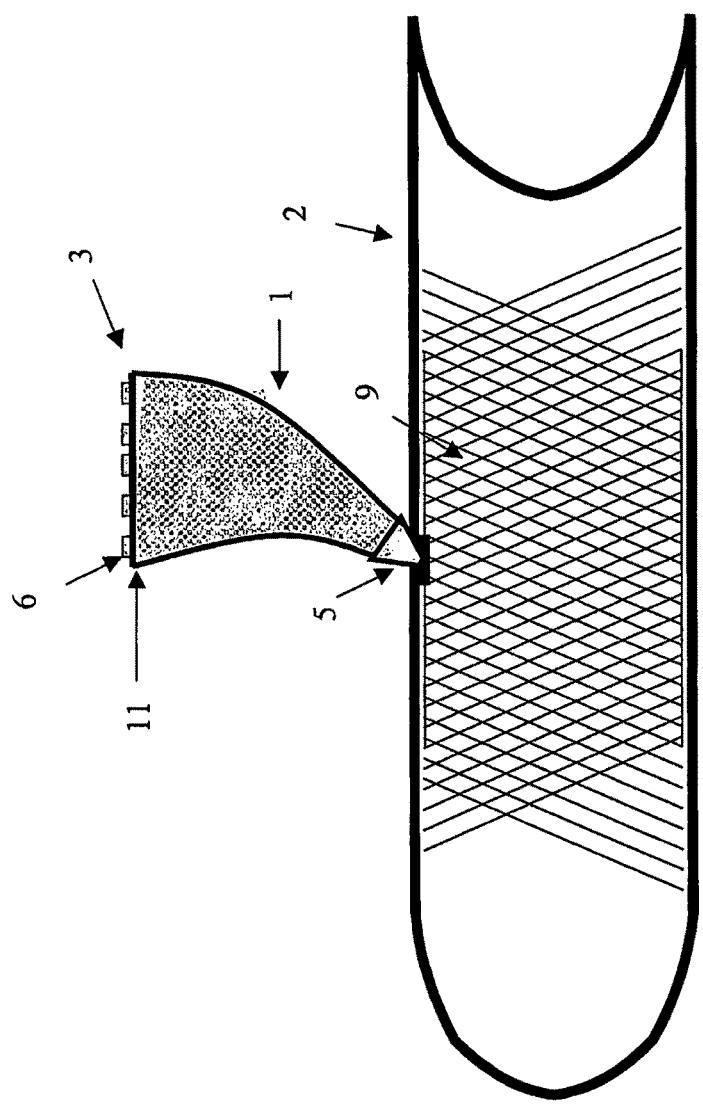
FIG. 5 shows one embodiment of the access device according to the invention integrated and fixed to a stent in a blood vessel.
Figure 6:
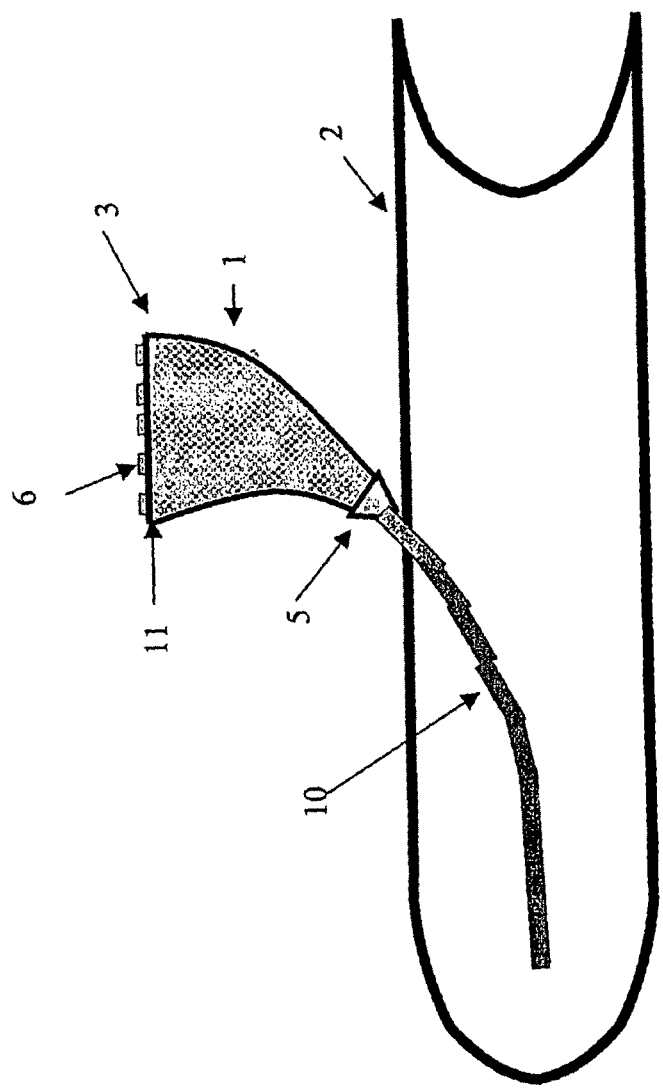
FIG. 6 shows one embodiment of the access device according to the invention with a permanent catheter, which enters the blood vessel directly.

Said positioning end (5) could be arranged to enter into the vessel system (2) in different ways. In one embodiment the positioning end (5) of the device is integrated with a kind of fixation mesh (7), which is fixated on the outer surface of a graft (8), see FIG. 4. In another embodiment the positioning end (5) is integrated with a fixation mesh in form of a stent (9) in a blood vessel (2), see FIG. 5. The guided pathway in the device according to the invention in combination with such fixation meshes guarantees that the needle will always find its right way for puncturing the graft or the vessel. In another access device according to the invention the positioning end (5) of the access device is connected with a permanent catheter (10), see FIG. 6 and FIG. 3 (left). Of course other combinations could be done with the access device according to the invention, a permanent catheter, a stent, and a graft.

The opening/closing mechanism in the access device according to the invention could in the simplest version be that the puncturing force opens the access and then closes the access when the force disappears, i.e. when the puncturing needle is removed, and then it could also include a valve.

Figure 1:
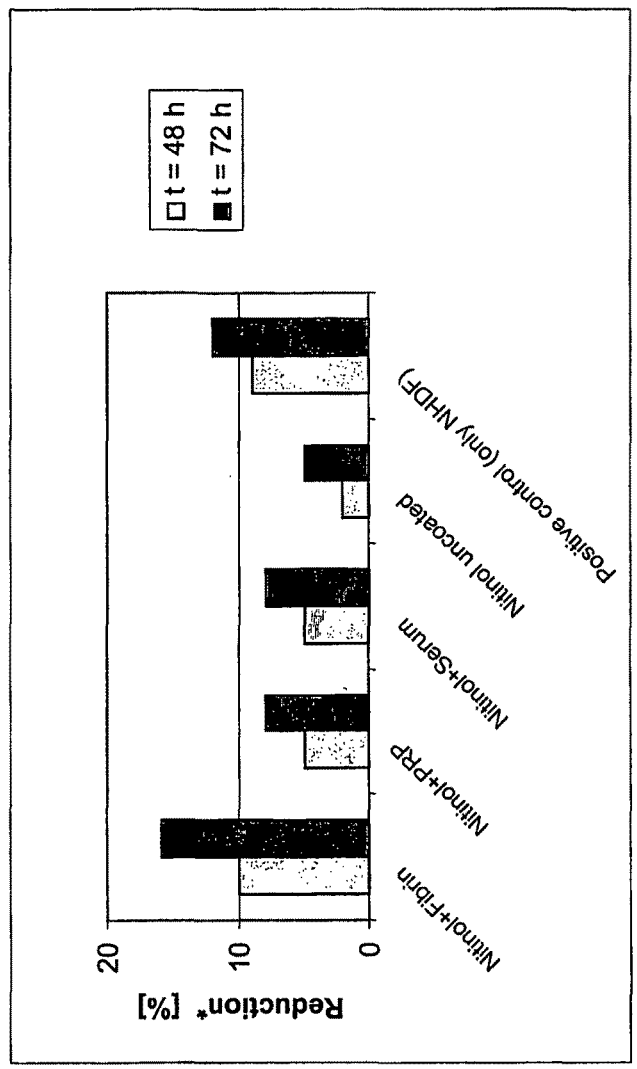
FIG. 1 shows the number of adhered normal human dermal fibroblasts on different coated nitinol plates measured as metabolic activity.
Figure 2:
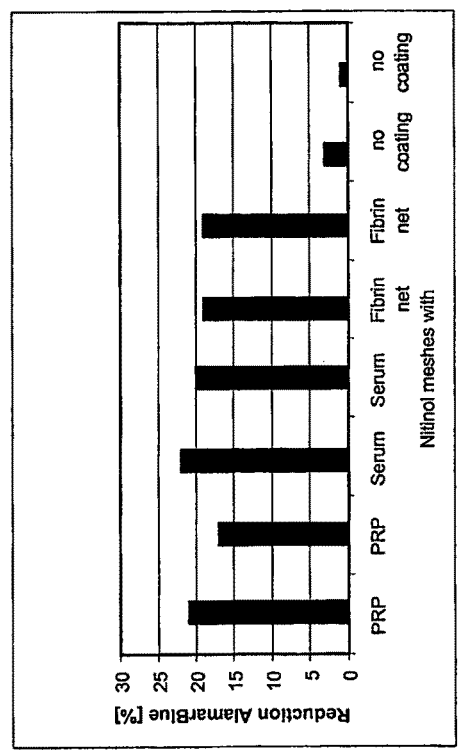
FIG. 2 shows the adherence of Normal Human Dermal Fibroblasts (NHDF) on different coated and non-coated Nitinol™ meshes measured as metabolic activity.

The puncturing could take place with specific needles that allow bending, whereby access to the vascular system is achieved over a tube or funnel type of connection ridging to the vascular system. In one embodiment the puncturing needles have blunt end to find or to get through the guided pathway without problems and not to damage the skeletal structure of the access system and not to cause too much injury/stress for the skin cells and small vessels. Below you find test methods and results in which we have verified and evaluated adhesion and proliferation of cell adhesion and growth on an access material which could be used in the access device according to the invention, the results of these tests are shown in FIG. 1 and FIG. 2.

Test Methods and Results

Verification and Evaluation of Adhesion and Proliferation

Description of AlamarBlue™ Test

AlamarBlue™ can be used as a proliferation and cytotoxicity indicator. The application of AlamarBlue™ requires the adjustment of different parameters to the scope of the test method. These parameters are AlamarBlue™ concentration, cell concentration, and time of incubation. For the definition of the measuring method several experiments were conducted and the time courses/kinetics of the reduction of AlamarBlue™ were evaluated.

Due to different experiments and microscopic controls of the cell population, the execution of the proliferation test method by means of AlamarBlue™ was specified, concerning the cell concentration as well as incubation periods and AlamarBlue™ concentrations, as follows:

TABLE 1

Parameter for proliferation verification of NHDF by means of AlamarBlue ™.

| Tissue culture plate [Number of wells] | Area per well [cm$^2$] | Conc. [Cells/well resp. Cells/ Test-substrate] | Volume of Culture-medium per well [ml] | Incubation period for Cell Suspension [h] | Volume of AlamarBlue-Solution per well [ml] | Incubation-period with AlamarBlue [h] |
|---|---|---|---|---|---|---|
| Petri-dish | 20 | 50 000 | 6 | 24 | 6 | 24 |
| 6 | 10 | 40 000-60 000 | 3 | 24 | 3 | 24 |
| 24 | 3.6 | 10 000-20 000 | 1 | 24 | 1 | 24 |
| 96 | 0.32 | 1 000-2 000 | 0.1 | 24 | 0.1 | 24 |

Description of the MTT-Test

The MTT Test is a rapid and sensitive colorimetric assay based on the formation of a coloured insoluble formazan salt. The amount of formazan produced is directly proportional to the cell number and therefore can be used to measure cell viability and proliferation. The assay is based on the capacity of the mitochondrial dehydrogenase enzymes to convert a yellow water-soluble tetrazolium salt (=MTT) into purple insoluble formazan product by a reduction reaction. This allows photometric analysis.

First different cell concentrations as well as different incubation periods of fibroblasts were examined to evaluate, in which scopes the settlement of the cells of surfaces can be determined.

The results of the colorimetric measurements are listed in Table 2.

TABLE 2

Proof of proliferation of NHDF by means of MTT, MTT added after 24, 48 and 72 hours.

| | Incubation period | | | | | | |
|---|---|---|---|---|---|---|---|
| | 24 | | 48 | | 72 | | |
| Concentration | Mean value OD | STD | Mean value OD | STD | Mean value OD | STD | n |
| 1000 | 0.012 | 0.002 | 0.006 | 0.003 | 0.022 | 0.003 | 8 |
| 2000 | 0.027 | 0.005 | 0.026 | 0.006 | 0.042 | 0.008 | 8 |
| 4000 | 0.052 | 0.015 | 0.053 | 0.009 | 0.091 | 0.004 | 8 |
| 6000 | 0.075 | 0.014 | 0.080 | 0.010 | 0.139 | 0.007 | 8 |
| 8000 | 0.108 | 0.018 | 0.095 | 0.013 | 0.160 | 0.010 | 8 |
| 15000 | 0.128 | 0.034 | 0.131 | 0.021 | 0.178 | 0.015 | 8 |

The measured values show, that the optical density is increasing with an ascending cell concentration. The cell cycle of fibroblast is around 20-24 h, in which the cells under optimal conditions should have been divided. Between the incubation periods of 24 h as well as 48 h are no significant changes of the measured values. After an incubation period of 72 h the cells have increased in number and proliferation signal. The reason therefore is, that the cells need an adaptation period after sowing before they accommodate to their regular cell cycle. For further proliferation examinations by means of MTT cell concentrations between 4000 and 6000 cells/100 µl will be sowed. In that scope it comes to clear signals, which are in the linear area of the OD (optical density)-courses.

Growth of fibroblasts on Nitinol™ (Results from Experiments)

Due to the mechanical properties and highly biocompatibility Nitinol™ was a primary choice for the first test for the base structure of the access device according to the invention. For further characterization of the materials biocompatibility examinations concerning cell adhesion and proliferation were carried out. Further, two functional elements need to be combined, mechanical and super elasticity, but still a sufficient and functional integration in the tissue environment must be achieved. The following experiments indicate possible solutions to the problem.

The material was coated with different human plasma components to get information about the influence of these coatings to cell adhesion and proliferation. One possibility of coating is to bring up fibrin nets on the base structure for simulating the wound healing process. The formation of fibrin is stimulated through the activation of coagulation in human platelet rich plasma (PRP). This goes on during a dynamic process, which has to be optimised concerning temperature, coagulation time, presence of calcium and platelet concentration of the plasma. Execution of the examined coatings are described in the following:

Platelet Rich Plasma (PRP):

Platelet count of the PRP is diluted with plasma to a total count of 100 000 platelets. The Nitinol™ samples are incubated in the adjusted PRP for 1 hour at 37° C./7% $CO_2$.

Plasma:

The Nitinol™ samples are incubated in plasma for 1 hour at 37° C./7% $CO_2$.

Fibrin Net Coating:

Adjusted PRP with a platelet count of 100 000 was added to the Nitinol™ samples and incubated for 30 min at 37° C./7% $CO_2$. Then the coagulation was started by addition of calcium chloride. 4 to 10 min after the coagulation process was started the formation of a 3-dimensional fibrin structure occurred and was then be stopped with sodium citrate at different levels.

Serum Coating:

Serum contains no coagulation factors. Therefore human whole blood is transferred in tubes, which are containing sterile glass beads. The glass beads known as initiators coagulation offer a great surface to the blood, which starts the coagulation procedure. The tubes with the whole blood were incubated for 1 hour at room temperature and 1 hour on ice. After centrifugation the supernatant, i.e. serum, were transferred into fresh tubes for storage or used directly for coating.

Collagen Coating:

Collagen is only soluble in an acid solution and polymerised at a neutral pH value. The collagen solution was added to the Nitinol™ samples, neutralised with sodium hydroxide and incubated for 1 hour at 37° C./7% $CO_2$.

For the adhesion and proliferation test methods, the coated and uncoated Nitinol™ meshes were transferred in test devices e.g. tubes or multi-dwell plates. All Nitinol™ samples were cleaned and steam sterilised before they were coated. There was given the cell concentration of fibroblast into the test device with the Nitinol samples. As positive controls for high proliferation rates fibroblasts in tissue culture plates were used.

The indicator solution containing AlamarBlue™ as non-toxic metabolic probe was brought on the test samples e.g. 24 hours and 48 hours after bringing the fibroblasts on the Nitinol™ samples and incubated for another 24 hours.

In FIG. 1 it is shown that the number of adhered fibroblasts on the substrate could be significantly increased through the coating with human plasma compound on the Nitinol™ material. This is shown by the higher reduction rates of AlamarBlue™. The best results were determined at Nitinol™ plates with a fibrin coating.

In FIG. 2 the proliferation of NHDF on Nitinol™ meshes are shown. After 15 days of proliferation, there are high reduction rates for cells on Nitinol™ meshes. That means that it is possible to proliferate/integrate normal human dermal fibroblast cells (NHDF), i.e. normal human skin cells, on the devices when a substructure is present on the device before introducing the NHDF cells.

However, after an incubation period of 15 days the reduction rate of Alamar Blue™ is nearly the same for Nitinol™ meshes as for Nitinol™ plates (except meshes without coating). That means that it is possible to proliferate/integrate human skin cells on the 3D-Nitinol™ device and the substructure can develop by different preparation methods.

It is also evident that the coating of the device is very important to get high proliferation rates of the fibroblasts on the implantation device, which is very important to achieve a total integration of the access device into the human body. Identification and Visualization of Fibroblast Cell Growth on Nitinol™ Meshes In order to more clearly identify and visualize the growth of fibroblasts on Nitinol™ meshes and to get a 3D-layout from the samples, specific immuno-staining procedure was performed and evaluated under the fluorescence microscope before confocal laser scanning microscopy (CLSM) was performed.

Figure 7:
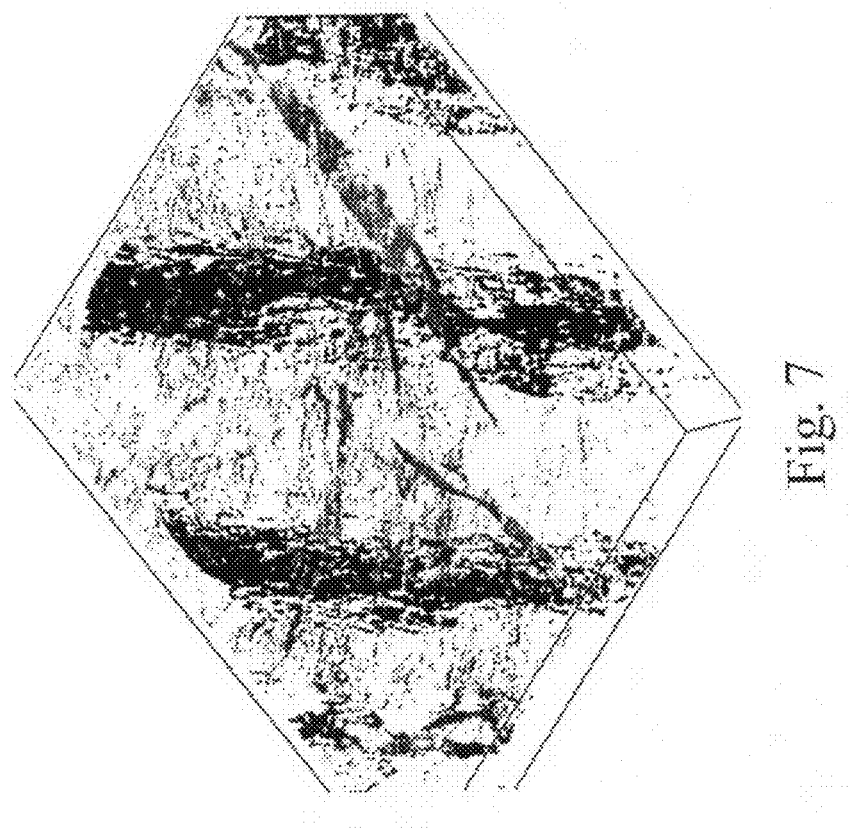
FIG. 7 shows that cells on Nitinol™ meshes proliferate well on fibrin coated Nitinol™ meshes analyzed by confocal laser scanning microscopy (Nitinol black, fibroblasts grey). This picture also depicts the cell integrating biofunctional 3-dimensional structure of the disclosed structures.

FIG. 7 shows that cells on Nitinol™ meshes proliferate well on fibrin coated Nitinol™ meshes (Nitinol black, fibroblasts grey)

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:

1. An implantable vascular access device comprising a shape memory base structure having openings, a substructure having openings, the substructure thereby being suitable for cell adhesion, cell engraftment and proliferation for use in transferring fluid into/out of a human or animal body, the shape memory base structure and the substructure permitting three-dimensional fixation and integration of cells on and within the access device, the shape memory base structure and the substructure together comprising a generally conical body having the shape memory base structure as a base of the generally conical body and adapted to receive a needle and a positioning end forming an apex of the generally conical body and adapted to position the end of said needle.

2. A device according to claim 1 wherein said substructure has filaments that are at least one of monofilaments and multifilaments.

3. A device according to claim 1, wherein said substructure is at least one of a biological polymeric substructure and a synthetic polymeric substructure.

4. A device according to claim 3, wherein said polymeric substructure comprises at least one of fibrin, plasma, platelet rich plasma, collagen, serum components, polyelectrolytes, hyaluronic acid, glycosaminoglycan, polyglucose, chitosan, alginate, polylactic acid, polyglycolic acid, polygluconic acid or mixtures thereof.

5. A device according to claim 1 wherein said shape memory base structure comprises at least one of a shape memory material and an elastic material.

6. A device according to claim 5, wherein said material is chosen from the group consisting of shape memory metallic alloy material, stainless steel, polymeric shape memory material, polygluconic acid, polyglycolic acid, polylactic acid, and collagen.

7. A device according to claim 1 wherein said base structure is at least one of braided, woven, foamed, and knitted.

8. A device according to claim 1 further comprising a mechanism for opening and closing to control fluid flow through the device.

9. A device according to claim 8, wherein said opening and closing mechanism is adapted to open when a needle is introduced into and bears upon said body portion positioning end.

10. A device according to claim 8, wherein said opening and closing mechanism is a valve.

11. A device according to claim 1 connected in the positioning end to a graft.

12. A device according to claim 1 connected in the positioning end to a stent.

13. A device according to claim 1 connected in the positioning end with a permanent catheter.

* * * * *

UNITED STATES PATENT AND TRADEMARK OFFICE
CERTIFICATE OF CORRECTION

| | | |
|---|---|---|
| PATENT NO. | : 10,251,979 B2 | Page 1 of 1 |
| APPLICATION NO. | : 11/993663 | |
| DATED | : April 9, 2019 | |
| INVENTOR(S) | : Schnell et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1391 days.

Signed and Sealed this
Tenth Day of December, 2019

Andrei Iancu
*Director of the United States Patent and Trademark Office*